(12) United States Patent
Mao et al.

(10) Patent No.: US 8,070,934 B2
(45) Date of Patent: *Dec. 6, 2011

(54) TRANSITION METAL COMPLEXES WITH (PYRIDYL)IMIDAZOLE LIGANDS

(75) Inventors: Fei Mao, Fremont, CA (US); Adam Heller, Austin, TX (US)

(73) Assignee: Abbott Diabetes Care Inc., Alameda, CA (US)

( * ) Notice: Subject to any disclaimer, the term of this patent is extended or adjusted under 35 U.S.C. 154(b) by 722 days.

This patent is subject to a terminal disclaimer.

(21) Appl. No.: 11/933,219

(22) Filed: Oct. 31, 2007

(65) Prior Publication Data

US 2008/0197026 A1 Aug. 21, 2008

Related U.S. Application Data

(63) Continuation-in-part of application No. 11/361,427, filed on Feb. 24, 2006, now Pat. No. 7,465,796, which is a continuation of application No. 10/714,835, filed on Nov. 14, 2003, now Pat. No. 7,074,308, which is a continuation of application No. 10/143,300, filed on May 9, 2002, now Pat. No. 6,676,816.

(60) Provisional application No. 60/290,537, filed on May 11, 2001.

(51) Int. Cl.
*G01N 27/327* (2006.01)
*C07H 15/00* (2006.01)

(52) U.S. Cl. ........... 205/777.5; 204/403.04; 204/403.14; 546/2; 548/101; 526/161

(58) Field of Classification Search ............. 204/403.04, 204/403.1, 403.14; 546/2; 526/161; 548/101; 205/777.5, 792

See application file for complete search history.

(56) References Cited

U.S. PATENT DOCUMENTS

| | | |
|---|---|---|
| 4,382,872 A | 5/1983 | Grinstead |
| 4,421,751 A | 12/1983 | Sundelin |
| 5,236,567 A | 8/1993 | Nanba et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,320,725 A | 6/1994 | Gregg et al. |
| 5,356,786 A | 10/1994 | Heller et al. |
| 5,378,628 A | 1/1995 | Gratzel et al. |
| 5,393,903 A | 2/1995 | Gratzel et al. |
| 5,410,059 A | 4/1995 | Fraser et al. |
| 5,437,999 A | 8/1995 | Diebold et al. |
| 5,463,057 A | 10/1995 | Graetzel et al. |
| 5,589,326 A | 12/1996 | Deng et al. |
| 5,593,852 A | 1/1997 | Heller et al. |
| 5,665,222 A | 9/1997 | Heller et al. |
| 5,683,832 A | 11/1997 | Bonhote et al. |
| 5,789,592 A | 8/1998 | Gratzel et al. |
| 5,804,049 A | 9/1998 | Chan |
| 5,846,702 A | 12/1998 | Deng et al. |
| 5,965,380 A | 10/1999 | Heller et al. |
| 5,972,199 A | 10/1999 | Heller et al. |
| 6,083,710 A | 7/2000 | Heller et al. |
| 6,103,033 A | 8/2000 | Say et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,175,752 B1 | 1/2001 | Say et al. |
| 6,245,988 B1 | 6/2001 | Gratzel et al. |
| 6,262,264 B1 | 7/2001 | Buck, Jr. et al. |
| 6,278,056 B1 | 8/2001 | Sugihara et al. |
| 6,294,062 B1 | 9/2001 | Buck, Jr. et al. |
| 6,338,790 B1 | 1/2002 | Feldman et al. |
| 6,352,824 B1 | 3/2002 | Buck, Jr. et al. |
| 6,605,200 B1 | 8/2003 | Mao et al. |
| 6,605,201 B1 | 8/2003 | Mao et al. |
| 6,616,819 B1 | 9/2003 | Liamos et al. |
| 6,676,816 B2 | 1/2004 | Mao et al. |
| 6,746,582 B2 | 6/2004 | Heller et al. |
| 7,074,308 B2 | 7/2006 | Mao et al. |
| 2003/0042137 A1 | 3/2003 | Mao et al. |
| 2003/0077772 A1 | 4/2003 | Shah et al. |
| 2003/0096997 A1 * | 5/2003 | Mao et al. .......................... 546/2 |
| 2004/0040840 A1 | 3/2004 | Mao et al. |
| 2004/0074785 A1 | 4/2004 | Holker et al. |

FOREIGN PATENT DOCUMENTS

EP 1 230 249 B1 6/2004

(Continued)

OTHER PUBLICATIONS

Abruna, et al., "Rectifying Interfaces Using Two-Layer Films of Electrochemically Polymerized Vinylpyridine and Vinylbipyridine Complexes of Ruthenium and Iron on Electrodes," *J. Am. Chem. Soc.*, vol. 103. No. 1. pp. 1-5 (Jan. 14.1981).

Cass et al., "Ferrocene-Mediated Enzyme Electrode for Amperometric Determination of Glucose," *Anal. Chem.*, vol. 56, No. 4, pp. 667-671 (Apr. 1984).

Cass et al., "Ferricinum Ion as an Electron Acceptor for Oxido-Reductases," *Electroanal. Chem.*, vol. 190, pp. 117-127 (1985).

Chen et al., "A Biocompatible Needle-Type Glucose Sensor Based on Platinum-Electroplated Carbon Electrode," *Applied Biochemistry and Biotechnology*, vol. 36, pp. 211-226 (1992).

Chen et al., "Amerpometric Needle-Type Glucose Sensor Based on a Modified Platinum Electrode with Diminished Response to Interfering Materials," *Analytica Chimica Acta*, vol. 265, pp. 5-14 (1992).

Csöregi et al., "Design, Characterization, and One-Point in Vivo Calibration of a Subcutaneously Implanted Glucose Electrode," *Anal. Chem.*, vol. 66, No. 19, pp. 3131-3138 (Oct. 1, 1994).

Csöregi et al., "On-Line Monitoring by Using Microdialysis Sampling and Amperometric Detection Based on 'Wired' Glucose Oxidase in Carbon Paste," *Mikrochim. Acta.*, vol. 121, pp. 31-40 (1995).

(Continued)

*Primary Examiner* — Kaj K Olsen

(74) *Attorney, Agent, or Firm* — Edward J. Baba; Khin Chin; Bozicevic, Field & Francis LLP

(57) ABSTRACT

Novel transition metal complexes of iron, cobalt, ruthenium, osmium, and vanadium are described. The transition metal complexes can be used as redox mediators in enzyme-based electrochemical sensors. The transition metal complexes include substituted or unsubstituted (pyridyl)imidazole ligands. Transition metal complexes attached to polymeric backbones are also described.

10 Claims, No Drawings

FOREIGN PATENT DOCUMENTS

| WO | 98/35225 | 8/1998 |
|---|---|---|
| WO | WO 99/03868 | 1/1999 |
| WO | 99/45375 | 9/1999 |
| WO | 99/45387 | 9/1999 |
| WO | 99/56613 | 11/1999 |
| WO | WO 99/59218 | 11/1999 |
| WO | 99/67628 | 12/1999 |
| WO | 00/20626 | 4/2000 |
| WO | WO 00/20626 | 4/2000 |
| WO | 01/36430 | 5/2001 |
| WO | 01/36660 | 5/2001 |
| WO | WO 01/36430 | 5/2001 |
| WO | WO 01/36660 | 5/2001 |
| WO | WO 03/098731 A1 | 11/2003 |

OTHER PUBLICATIONS

Degani et al., Direct Electrical Communication Between Chemically Modified Enzymes and Metal Electrodes. 1. Electron Transfer from Glucose Oxidase to Metal Electrodes via Electron Relays, Bound Covalently to the Enzyme. *J. Phys. Chem.*. vol. 91. No. 6. pp. 1285-1289 (1987).

Degani et al., "Direct Electrical Communication between Chemically Modified Enzymes and Metal Electrodes. 2. Methods for Bonding Electron-Transfer Relays to Glucose Oxidase and D-Amino-Acid Oxidase." *J. Am. Chem. Soc.*. vol. 110. No. 8. pp. 2615-2620 (1988).

Degani et al., "Electrical Communication Between Redox Centers of Glucose Oxidase and Electrodes Via Electrostatically and Covalently Bound Redox Polymers," *J. Am. Chem. Soc.*, vol. 111, pp. 2357-2358 (1989).

Dicks, "Ferrocene Modified Polypyrrole with Immobilised Glucose Oxidase and its Application in Amperometric Glucose Microbiosensors," *Ann. Biol. Clin.*, vol. 47, pp. 607-619 (1989).

Doherty et al., "The Effect of the Nature of the Polymer Backbone on the Stability and the Analytical Response of Polymer-Modified Electrodes," *Electroanalysis*, (1995), vol. 7, No. 4, pp. 333-339.

Fieselmann, et al., "Synthesis, Electron Paramagnetic Resonance, and Magnetic Studies on Binuclear Resonance . . . ", *Inorganic Chemistry*, vol. 17, No. 8, pp. 2078-2084 (1978).

Fischer et al., "Intramolecular Electron Transfer Mediated by 4,4'-Bipyridine and Related Bridging Groups," *J. Am. Chem. Soc.*, vol. 98, No. 18, pp. 5512-5517 (Sep. 1, 1976).

Foulds et al., "Enzyme Entrapment in Electrically Conducting Polymers," *J. Chem. Soc., Faraday Trans 1.*, vol. 82, pp. 1259-1264 (1986).

Foulds et al., "Immobilization of Glucose Oxidase in Ferrocene-Modified Pyrrole Polymers," *anal. Chem.*, vol. 60, No. 22, pp. 2473-2478 (Nov. 15, 1998).

Gholamkhass et al., J. Phys. Chem, 101, 1997, pp. 9010-9021.

Greggs et al., "Cross-Linked Redox Gels Containing Glucose Oxidase for Amperometric Biosensor Applications," *Analytical Chemistry*, vol. 62, No. 3, pp. 258-263 (Feb. 1, 1990).

Gregg et al., "Redox Polymer Films Containing Enzymes. 1. A Redox-Conducting Epoxy Cement: Synthesis, Characterization, and Electrocatalytic Oxidation of Hydroquinone," *J. Phys. Chem.*, vol. 95, No. 15. pp. 5970-5975 (1991).

Haga, "Synthesis and Protonation-Deprotanation Reactions of Ruthenium(II) Complexes Containing 2,2' -Bibenzimidazole and Related Ligands," *Inorganica Chimica Acta*, vol. 75, pp. 29-35 (1983).

Hale et al., "A New Class of Amperometric Biosensor Incorporating a Polymeric Electron-Transfer Mediator," *J. Am. Chem. Soc.*, vol. 111, No. 9, pp. 3482-3484 (1989).

Heller et al., "Electrical Connection of Enzyme Redox Centers to Electrodes," *J. Phys. Chem.*, vol. 96, No. 9, pp. 3579-3587 (1992).

Heller, "Electrical Wiring of Redox Enzymes," *Acc. Chem. Res.*, vol. 23, No. 5, pp. 129-134 (1990).

Ianniello et al., "Immobilized Enzyme Chemically Modified Electrode as an Amperometric Sensor," *Anal. Chem.*, vol. 53, No. 13, pp. 2090-2095 (Nov. 1981).

Ikeda et al., "Glucose Oxidase-Immobilized Benzoquinone-Carbon Paste Electrode as a Glucose Sensor," *Agric. Biol. Chem.*, vol. 49, No. 2, (1 page—Abstract only) (1985).

Jönsson et al., "An Amperometric Glucose Sensor Made by Modification of a Graphite Electrode Surface with Immobilized Glucose Oxidase and Adsorbed Mediator," *Biosensors*, vol. 1, pp. 355-368 (1985).

Katakis et al., "L-α-Glycerophosphate and L-Lactate Electrodes Based on the Electrochemical 'Wiring' of Oxidases," *Analytical Chemistry*, vol. 64, No. 9, pp. 1008-1013 (May 1, 1992).

Katakis et al., "Electrostatic Control of the Electron Transfer Enabling Binding of Recombinant Glucose Oxidase and Redox Polyelectrolytes," *J. Am. Chem. Soc.*, vol. 116, No. 8, pp. 3617-3618 (1994).

Kenausis et al., "'Wiring' of Glucose Oxidase and Lactate Oxidase Within a Hydrogel Made with Poly(Vinyl Pyridine) . . . ." *J. Chem. Soc., Faraday Trans.*, vol. 92, No. 20, pp. 4131-4136 (1996).

Maidan et al., "Elimination of Electrooxidizable Interferant-Produced Currents in Amperometric Biosensors," *Analytical Chemistry*, vol. 64, No. 23, pp. 2889-2896 (Dec. 1, 1992).

Majumdar et al., "Biimidazole Complexes of ML22+[M=Ru or L=2-(Phenylazo)-Pyridine]. Synthesis, Structure and Redox Properties of Mono- and Di-Nuclear Complexes," *J. Chem. Soc. Dalton Trans.*, 1998. pp. 1569-1574.

Ohara et al., "'Wired' Enzyme Electrodes for Amperometric Determination of Glucose or Lactate in the Presence of Interfering Substances," *Analytical Chemistry*, vol. 66, No. 15, pp. 2451-2457 (Aug. 1, 1994).

Ohara, "Osmium Bipyridyl Redox Polymers Used in Enzyme Electrodes," *Platinum Metals Rev.*, vol. 39, No. 2, pp. 54-62 (Apr. 1995).

Ohara et al., "Glucose Electrodes Based on Cross-Linked $[Os(bpy)_2Cl]^{+/2+}$ Complexed Poly(1-vinylimadazole) Films," *Analytical Chemistry*, vol. 65, No. 23, pp. 3512-3516 (Dec. 1, 1993).

Ohara et al., "Glucose Electrodes Based on Cross-Linked $[Os(bpy)_2Cl]^{+/2+}$ Complexed Poly(1-vinylimadazole) Films," Department of Chemical Engineering University of Texas at Austin, pp. 182-183.

Pickup, J. "Potentially-Implantable, Amperometric Glucose Sensors with Mediated Electron Transfer: Improving the Operating Stability," *Biosensors*, vol. 4, No. 2, (1 page—Abstract only) (1989).

Pishko et al., "Amperometric Glucose Microelectrodes Prepared Through Immobilization of Glucose Oxidase in Redox Hydrogels," *Anal. Chem.*, vol. 63, No. 20, pp. 2268-2272 (Oct. 15, 1991).

Pollak et al., "Enzyme Immobilization by Condensation Copolymerization into Cross-Linked Polyacrylamide Gels," *J. Am. Chem. Soc.*, vol. 102, No. 20, pp. 6324-6336 (1980).

Reeder et al., "Solution-State Spin-Equilibrium Properties of the Tris[2-(2-Pyridyl)imidazole]iron(II) and Tris[2-92-Pyridyl)benzimidazole]iron(II) Cations," *Inorganic Chemistry*, vol. 17, No. 4, pp. 1071-1075 (1978).

Sasso et al., "Electropolymerized 1,2-Diaminobenzene as a Means to Prevent Interferences and Fouling and to Stabilize Immobilized Enzyme in Electrochemical Biosensors," *Anal. Chem.*, vol. 62, No. 11, pp. 1111-1117 (Jun. 1, 1990).

Schalkhammer et al., "Electrochemical Glucose Sensors on Permselective Non-Conducting Substituted Pyrrole Polymers," *Sensors and Actuators*, vol. B4, pp. 273-281 (1991).

Taylor et al., "'Wiring' of Glucose Oxidase Within a Hydrogel Made with Polyvinyl Imidazole Complexed with [(Os-4,4'-Dimethoxy-2,2'-Bipyridine)Cl]$^{+/2+}$," *Journal of Electroanalytical Chemistry*, vol. 396. pp. 511-515 (1995).

Trojanowicz et al., "Enzyme Entrapped Polypyrrole Modified Electrode for Flow-Injection Determination of Glucose," *Biosensors & Bioelectronics*, vol. 5, pp. 149-156 (1990).

Ye et al., "High Current Density 'Wired' Quinoprotein Glucose Dehydrogenase Electrode," *Anal. Chem.*, vol. 65, No. 3, pp. 238-241 (Feb. 1, 1993).

Yildiz et al., "Evaluation of an Improved Thin-Layer Electrode," *Analytical Chemistry*, vol. 40. No. 7, pp. 1018-1024 (Jun. 1968).

Yu et al., Macromolecules, 1999, 32, pp. 5251-5256.

Communication Pursuant to Article 96(2), European Patent Application No. 00 978 573.4—2117 for TheraSense, Inc. dated Dec. 2, 2003, 9 pages.

Communication Pursuant to Article 96(2), European Patent Application No. 00 978 573.4—2117 for TheraSense, Inc. dated May 31, 2005, 4 pages.

Calvert et al., "Synthetic and Mechanistic Investigations of the Reductive Electrochemical Polymerization of Vinyl-Containing Complexes of Iron (II), Ruthenium(II), and Osmium(II)," Inorganic Chemistry, vol. 22, No. 15, 1983, pp. 2151-2162.

Schmehl et al., "The Effect of Redox Site Concentration on the Rate of Mediated Oxidation of Solution Substrates by a Redox Copolymer Film," J. Electroanal. Chem. 152, 1983, pp. 97-109.

Surridge et al., Electron and Counterion Diffusion Constants in Mixed-Valent Polymeric Osmium Bipyridine Films, The Journal of Physical Chemistry, vol. 98, No. 3, 1994, pp. 917-923.

Surridge et al., Site Dilution of Osmium Polypyridine Complexes in Three Electron-Hopping Conductive Polymer Films on Electrodes by Electrochemical Copolymerization of Osmium with Ruthenium and with Zinc Complexes, Inorganic Chemistry, vol. 29, No. 24, 1990, pp. 4950-4955.

Chiswell, et al., "Bidentate Chelate Compounds. III. Metal Complexes of Some Pyridyl-imidazole Derivatives" Inorg. Chem., 1964, 3 (1), 110-114.

* cited by examiner

US 8,070,934 B2

TRANSITION METAL COMPLEXES WITH (PYRIDYL)IMIDAZOLE LIGANDS

CROSS-REFERENCE TO RELATED APPLICATIONS

This application is a continuation-in-part of U.S. patent application Ser. No. 11/361,427 filed on Feb. 24, 2006, which issued as U.S. Pat. No. 7,465,796, which is a continuation of U.S. patent application Ser. No. 10/714,835, filed on Nov. 14, 2003, which issued as U.S. Pat. No. 7,074,308, which is a continuation of U.S. patent application Ser. No. 10/143,300, filed May 9, 2002, which issued as U.S. Pat. No. 6,676,816 and claims the benefit of U.S. Provisional Patent Application No. 60/290,537, filed on May 11, 2001. Each of the foregoing applications is incorporated herein in its entirety by this reference.

FIELD OF THE INVENTION

This invention relates to transition metal complexes with (pyridyl)imidazole ligands. In addition, the invention relates to the preparation of the transition metal complexes and to the use of the transition metal complexes as redox mediators.

BACKGROUND OF THE INVENTION

Enzyme-based electrochemical sensors are widely used in the detection of analytes in clinical, environmental, agricultural and biotechnological applications. Analytes that can be measured in clinical assays of fluids of the human body include, for example, glucose, lactate, cholesterol, bilirubin and amino acids. Levels of these analytes in biological fluids, such as blood, are important for the diagnosis and the monitoring of diseases.

Electrochemical assays are typically performed in cells with two or three electrodes, including at least one measuring or working electrode and one reference electrode. In three electrode systems, the third electrode is a counter-electrode. In two electrode systems, the reference electrode also serves as the counter-electrode. The electrodes are connected through a circuit, such as a potentiostat. The measuring or working electrode is a non-corroding carbon or metal conductor. Upon passage of a current through the working electrode, a redox enzyme is electrooxidized or electroreduced. The enzyme is specific to the analyte to be detected, or to a product of the analyte. The turnover rate of the enzyme is typically related (preferably, but not necessarily, linearly) to the concentration of the analyte itself, or to its product, in the test solution.

The electrooxidation or electroreduction of the enzyme is often facilitated by the presence of a redox mediator in the solution or on the electrode. The redox mediator assists in the electrical communication between the working electrode and the enzyme. The redox mediator can be dissolved in the fluid to be analyzed, which is in electrolytic contact with the electrodes, or can be applied within a coating on the working electrode in electrolytic contact with the analyzed solution. The coating is preferably not soluble in water, though it may swell in water. Useful devices can be made, for example, by coating an electrode with a film that includes a redox mediator and an enzyme where the enzyme is catalytically specific to the desired analyte, or its product. In contrast to a coated redox mediator, a diffusional redox mediator, which can be soluble or insoluble in water, functions by shuttling electrons between, for example, the enzyme and the electrode. In any case, when the substrate of the enzyme is electrooxidized, the redox mediator transports electrons from the substrate-reduced enzyme to the electrode; and when the substrate is electroreduced, the redox mediator transports electrons from the electrode to the substrate-oxidized enzyme.

Recent enzyme-based electrochemical sensors have employed a number of different redox mediators such as monomeric ferrocenes, quinoid compounds including quinines (e.g., benzoquinones), nickel cyclamates, and ruthenium amines. For the most part, these redox mediators have one or more of the following limitations: the solubility of the redox mediators in the test solutions is low, their chemical, light, thermal, and/or pH stability is poor, or they do not exchange electrons rapidly enough with the enzyme or the electrode or both. Some mediators with advantageous properties are difficult to synthesize. Additionally, the redox potentials of some of these reported redox mediators are so oxidizing that at the potential at which the reduced mediator is electrooxidized on the electrode, solution components other than the analyte are also electrooxidized. Some other of these reported redox mediators are so reducing that solution components, such as, for example, dissolved oxygen, are also rapidly electroreduced. As a result, the sensor utilizing the mediator is not sufficiently specific.

SUMMARY OF THE INVENTION

The present invention is directed to novel transition metal complexes. The present invention is also directed to the use of the complexes as redox mediators. The preferred redox mediators typically exchange electrons rapidly with enzymes and electrodes, are stable, can be readily synthesized, and have a redox potential that is tailored for the electrooxidation of analytes, such as glucose for example.

One embodiment of the invention is a transition metal complex having the general formula set forth below.

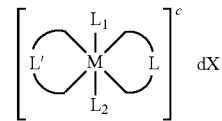

In this general formula, M is cobalt, iron, ruthenium, osmium, or vanadium: c is an integer selected from −1 to −5, 0, or +1 to +5 indicating a positive, neutral, or negative charge; X represents at least one counter ion; d is an integer from 0 to 5 representing the number of counter ions, X; L and L' are independently selected from the group consisting of:

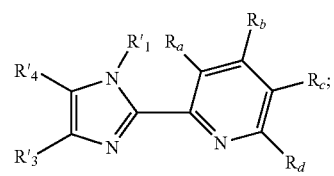

and $L_1$ and $L_2$ are other ligands. In the formula for L and L', $R'_1$ is a substituted or an unsubstituted alkyl, alkenyl, or aryl group. Generally, $R'_3$, $R'_4$, $R_a$, $R_b$, $R_c$, and $R_d$ are independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl.

The transition metal complexes of the present invention are effectively employed as redox mediators in electrochemical sensors, given their very fast kinetics. More particularly, when a transition metal complex of this invention is so employed, rapid electron exchange between the transition metal complex and the enzyme and/or the working electrode in the sensor device occurs. This electron exchange is sufficiently rapid to facilitate the transfer of electrons to the working electrode that might otherwise be transferred to another electron scavenger in the system. The fast kinetics of the mediator is generally enhanced when $L_2$ of a mediator of the formula provided above is a negatively charged ligand.

The transition metal complexes of the present invention are also quite stable. For example, when such a complex is used as a mediator in an electrochemical sensor, the chemical stability is generally such that the predominant reactions in which the mediator participates are the electron-transfer reaction between the mediator and the enzyme and the electrochemical redox reaction at the working electrode. The chemical stability may be enhanced when a mediator of the formula provided above, wherein $L_2$ is a negatively charged ligand, has a "bulky" chemical ligand, $L_1$, that shields the redox center, M, and thereby reduces undesirable chemical reactivity beyond the desired electrochemical activity.

The electrochemical stability of the transition metal complexes of the present invention is also quite desirable. For example, when such a complex is used as a mediator in an electrochemical sensor, the mediator is able to operate in a range of redox potentials at which electrochemical activity of common interfering species is minimized and good kinetic activity of the mediator is maintained.

Thus, the present invention provides novel transition metal complexes that are particularly useful as redox mediators in electrochemical sensing applications. The advantageous properties and characteristics of the transition metal complexes of the present invention make them ideal candidates for use in the electrochemical sensing of glucose, an application of particular importance in the treatment of diabetes in human populations.

DETAILED DESCRIPTION

When used herein, the definitions set forth below in quotations define the stated term.

The term "alkyl" includes linear or branched, saturated aliphatic hydrocarbons. Examples of alkyl groups include methyl, ethyl, n-propyl, isopropyl, n-butyl, tert-butyl and the like. Unless otherwise noted, the term "alkyl" includes both alkyl and cycloalkyl groups.

The term "alkoxy" describes an alkyl group joined to the remainder of the structure by an oxygen atom. Examples of alkoxy groups include methoxy, ethoxy, n-propoxy, isopropoxy, butoxy, tert-butoxy, and the like. In addition, unless otherwise noted, the term 'alkoxy' includes both alkoxy and cycloalkoxy groups.

The term "alkenyl" describes an unsaturated, linear or branched aliphatic hydrocarbon having at least one carbon-carbon double bond. Examples of alkenyl groups include ethenyl, 1-propenyl, 2-propenyl, 1-butenyl, 2-methyl-1-propenyl, and the like.

A "reactive group" is a functional group of a molecule that is capable of reacting with another compound to couple at least a portion of that other compound to the molecule. Reactive groups include carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. Activated esters, as understood in the art, generally include esters of succinimidyl, benzotriazolyl, or aryl substituted by electron-withdrawing groups such as sulfo, nitro, cyano, or halo groups; or carboxylic acids activated by carbodimides.

A "substituted" functional group (e.g., substituted alkyl, alkenyl, or alkoxy group) includes at least one substituent selected from the following: halogen, alkoxy, mercapto, aryl, alkoxycarbonyl, alkylaminocarbonyl, dialkylaminocarbonyl, —OH, —NH$_2$, alkylamino, dialkylamino, trialkylammonium, alkanoylamino, arylcarboxamido, hydrazino, alkylthio, alkenyl, and reactive groups.

A "biological fluid" is any body fluid or body fluid derivative in which the analyte can be measured, for example, blood, interstitial fluid, plasma, dermal fluid, sweat, and tears.

An "electrochemical sensor" is a device configured to detect the presence of or measure the concentration or amount of an analyte in a sample via electrochemical oxidation or reduction reactions. These reactions typically can be transduced to an electrical signal that can be correlated to an amount or concentration of analyte.

A "redox mediator" is an electron transfer agent for carrying electrons between an analyte or an analyte-reduced or analyte-oxidized enzyme and an electrode, either directly, or via one or more additional electron transfer agents. Redox mediators that include a polymeric backbone may also be referred to as "redox polymers".

"Electrolysis" is the electrooxidation or electroreduction of a compound either directly at an electrode or via one or more electron transfer agents (e.g., redox mediators or enzymes).

The term "reference electrode" includes both a) reference electrodes and b) reference electrodes that also function as counter electrodes (i.e., counter/reference electrodes), unless otherwise indicated.

The term "counter electrode" includes both a) counter electrodes and b) counter electrodes that also function as reference electrodes (i.e., counter/reference electrodes), unless otherwise indicated.

Generally, the present invention relates to transition metal complexes of iron, cobalt, ruthenium, osmium, and vanadium having (pyridyl)imidazole ligands. The invention also relates to the preparation of the transition metal complexes and to the use of the transition metal complexes as redox mediators. In at least some instances, the transition metal complexes have one or more of the following characteristics: redox potentials in a particular range, the ability to exchange electrons rapidly with electrodes, the ability to rapidly transfer electrons to or rapidly accept electrons from an enzyme to accelerate the kinetics of electrooxidation or electroreduction of an analyte in the presence of an enzyme or another analyte-specific redox catalyst. For example, a redox mediator may accelerate the electrooxidation of glucose in the presence of glucose oxidase or PQQ-glucose dehydrogenase, a process that can be useful for the selective assay of glucose in the presence of other electrochemically oxidizable species. Some embodiments of the invention may be easier or more cost-effective to make synthetically or use more widely available or more cost-effective reagents in synthesis than other transition metal redox mediators.

Compounds having Formula 1, set forth below, are examples of transition metal complexes of the present invention.

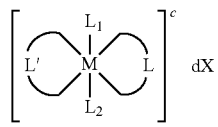

M is a transition metal and is typically iron, cobalt, ruthenium, osmium, or vanadium. Ruthenium and osmium are particularly suitable for redox mediators.

L and L' are each bidentate, substituted or unsubstituted 2-(2-pyridyl)imidazole ligands having the Structure 2 set forth below.

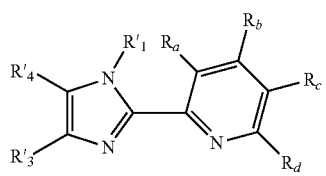

In Structure 2, $R'_1$ is a substituted or an unsubstituted aryl, alkenyl, or alkyl. Generally, $R'_1$ is a substituted or an unsubstituted C1-C12 alkyl or alkenyl, or an aryl, such as phenyl, optionally substituted with a substituent selected from a group consisting of —Cl, —F, —CN, amino, carboxy, C1-C6 alkyl, C1-C6 alkylthio, C1-C6 alkylamino, C1-C6 dialkylamino, C1-C6 alkylaminocarbonyl, C1-C6 alkoxy, C1-C6 alkoxycarbonyl, and C1-C6 alkylcarboxamido. $R'_1$ is typically methyl or a C1-C12 alkyl that is optionally substituted with a reactive group, or an aryl optionally substituted with C1-C2 alkyl, C1-C2 alkoxy, —Cl, or —F.

Generally, $R'_3$, $R'_4$, $R_a$, $R_b$, $R_c$, and $R_d$ are independently —H, —F, —Cl, —Br, —I, —NO$_2$, —CN, —CO$_2$H, —SO$_3$H, —NHNH$_2$, —SH, —OH, —NH$_2$, substituted or unsubstituted alkoxylcarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl. Alternatively, $R_c$ and $R_d$ in combination and/or $R'_3$ and $R'_4$ in combination can form a saturated or unsaturated 5- or 6-membered ring. Typically, the alkyl and alkoxy portions are C1 to C12. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. Generally, $R'_3$, $R'_4$, $R_a$, $R_b$, $R_c$ and $R_d$ are independently —H or unsubstituted alkyl groups. Typically, $R_a$ and $R_c$ are —H and $R'_3$, $R'_4$, $R_b$, and $R_d$ are —H or methyl.

Preferably, the L and L' ligands are the same. Herein, references to L and L' may be used interchangeably.

In Formula 1, c is an integer indicating the charge of the complex. Generally, c is an integer selected from −1 to −5 or +1 to +5 indicating a positive or negative charge or 0 indicating a neutral charge. For a number of osmium complexes, c is +1, +2, or +3.

X represents counter ion(s). Examples of suitable counter ions include anions, such as halide (e.g., fluoride, chloride, bromide or iodide), sulfate, phosphate, hexafluorophosphate, and tetrafluoroborate, and cations (preferably, monovalent cations), such as lithium, sodium, potassium, tetralkylammonium, and ammonium. Preferably, X is a halide, such as chloride. The counter ions represented by X are not necessarily all the same.

d represents the number of counter ions and is typically from 0 to 5.

$L_1$ and $L_2$ are ligands attached to the transition metal via a coordinative bond. $L_1$ and $L_2$ are monodentate ligands, at least one of which is a negatively charged monodentate ligand. While $L_1$ and $L_2$ may be used interchangeably, $L_2$ is generally referred to as a negatively charged ligand merely by way of convenience. Herein, the term "negatively charged ligand" is defined as a ligand in which the coordinating atom itself is negatively charged so that on coordination to a positively charged metal, the negative charge is neutralized. For example, a halide such as chloride or fluoride meets the present definition while a pyridine ligand bearing a negatively charged sulfonate group does not because the sulfonate group does not participate in coordination. Examples of negatively charged ligands include, but are not limited to, —F, —Cl, —Br, —I, —CN, —SCN, —OH, alkoxy, alkylthio, and phenoxide. Typically, the negatively charged monodentate ligand is a halide.

Examples of other suitable monodentate ligands include, but are not limited to, H$_2$O, NH$_3$, alkylamine, dialkylamine, trialkylamine, or heterocyclic compounds. The alkyl or aryl portions of any of the ligands are optionally substituted by —F, —Cl, —Br, —I, alkylamino, dialkylamino, trialkylammonium (except on aryl portions), alkoxy, alkylthio, aryl, or a reactive group. Any alkyl portions of the monodentate ligands generally contain 1 to 12 carbons. More typically, the alkyl portions contain 1 to 6 carbons. In other embodiments, the monodentate ligands are heterocyclic compounds containing at least one nitrogen, oxygen, or sulfur atom. Examples of suitable heterocyclic monodentate ligands include imidazole, pyrazole, oxazole, thiazole, triazole, pyridine, pyrazine and derivatives thereof. Suitable heterocyclic monodentate ligands include substituted and unsubstituted imidazole and substituted and unsubstituted pyridine having the general Formulas 3 and 4, respectively, as set forth below.

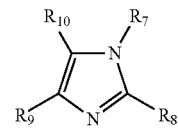

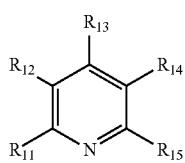

With regard to Formula 3, $R_7$ is generally a substituted or unsubstituted alkyl, alkenyl, or aryl group. Generally, $R_7$ is a substituted or unsubstituted C1 to C12 alkyl or alkenyl, or an aryl, such as phenyl, optionally substituted with a substituent selected from a group consisting of —Cl, —F, —CN, amino, carboxy, C1-C6 alkyl, C1-C6 alkylthio, C1-C6 alkylamino, C1-C6 dialkylamino, C1-C6 alkylaminocarbonyl, C1-C6 alkoxy, C1-C6 alkoxycarbonyl, and C1-C6 alkylcarboxamido. $R_7$ is typically methyl or a C1-C12 alkyl that is optionally substituted with a reactive group, or an aryl optionally substituted with C1-C2 alkyl, C1-C2 alkoxy, —Cl, or —F.

Generally, $R_8$, $R_9$ and $R_{10}$ are independently —H, —F, —Cl, —Br, —I, —$NO_2$, —CN, —$CO_2H$, —$SO_3H$, —$NH_2$, —SH, —OH, —$NH_2$, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl. Alternatively, $R_9$ and $R_{10}$, in combination, form a fused 5- or 6-membered ring that is saturated or unsaturated. The alkyl portions of the substituents generally contain 1 to 12 carbons and typically contain 1 to 6 carbon atoms. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. In some embodiments, $R_8$, $R_9$ and $R_{10}$ are —H or substituted or unsubstituted alkyl. Preferably, $R_8$, $R_9$ and $R_{10}$ are —H.

With regard to Formula 4, $R_{11}$, $R_{12}$, $R_{13}$, $R_{14}$ and $R_{15}$ are independently —H, —F, —Cl, —Br, —I, —$NO_2$, —CN, —$CO_2H$, —OH, —$NH_2$, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl. The alkyl or aryl portions of any of the substituents are optionally substituted by —F, —Cl, —Br, —I, alkylamino, dialkylamino, trialkylammonium (except for aryl portions), alkoxy, alkylthio, aryl, or a reactive group. Generally, $R_{11}$, $R_{12}$, $R_{13}$, $R_{14}$ and $R_{15}$ are —H, methyl, C1-C2 alkoxy, C1-C2 alkylamino, C2-C4 dialkylamino, or a C1-C6 lower alkyl substituted with a reactive group.

One example includes $R_{11}$ and $R_{15}$ as —H, $R_{12}$ and $R_{14}$ as the same and —H or methyl, and $R_{13}$ as —H, C1 to C12 alkoxy, —$NH_2$, C1 to C12 alkylamino, C2 to C24 dialkylamino, hydrazino, C1 to C12 alkylhydrazino, hydroxylamino, C1 to C12 alkoxyamino, C1 to C12 alkylthio, or C1 to C12 alkyl. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group.

Examples of suitable transition metal complexes include [Os[1-methyl-2-(2-pyridyl)imidazole]$_2$(1-methylimidazole)Cl]$^{2+}$2Cl— (also written as [Os(Py-MIM)$_2$(MIM)Cl]$^{2+}$ 2Cl—) where $L_1$ is

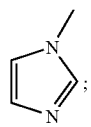

$L_2$ is Cl; c is ±2; d is 2; X is Cl—; and L and L' are

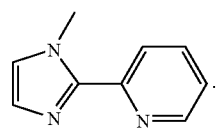

The transition metal complexes of Formula 1 also include transition metal complexes that are coupled to a polymeric backbone through one or more of L, L', $L_1$, and $L_2$. In some embodiments, the polymeric backbone has at least one functional group that acts as a ligand of the transition metal complex. Such polymeric backbones include, for example, poly (4-vinylpyridine) and poly(N-vinylimidazole) in which the pyridine and imidazole groups, respectively, can act as monodentate ligands of the transition metal complex. In other embodiments, the transition metal complex can be the reaction product between a reactive group on a precursor polymer and a reactive group on a ligand of a precursor transition metal complex (such as complex of Formula 1 where one of L, L', $L_1$, and $L_2$ includes a reactive group, as described above). Suitable precursor polymers include, for example, poly (acrylic acid) (Formula 7), styrene/maleic anhydride copolymer (Formula 8), methylvinylether/maleic anhydride copolymer (GANTREZ polymer) (Formula 9), poly (vinylbenzylchloride) (Formula 10), poly(allylamine) (Formula II), polylysine (Formula 12), carboxy-poly(vinylpyridine) (Formula 13), and poly(sodium 4-styrene sulfonate) (Formula 14). The numbers n, n' and n" appearing variously in these formulas may vary widely. Merely by way of example, in Formula 13, [n'/(n'+n")]×100% is preferably from about 5% to about 15%.

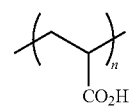

7

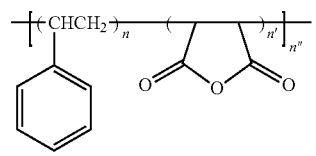

8

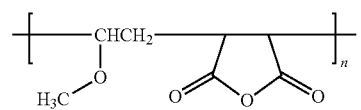

9

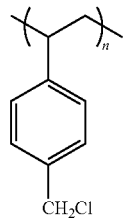

10

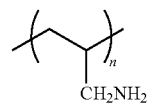

11

12

13

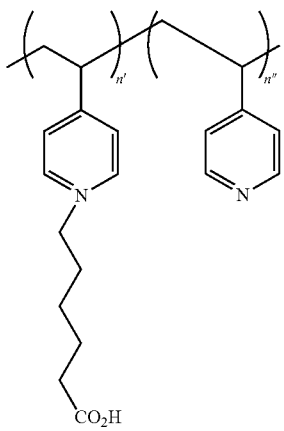

14

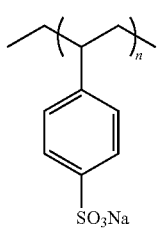

Alternatively, the transition metal complex can have one or more reactive group(s) for immobilization or conjugation of the complexes to other substrates or carriers, examples of which include, but are not limited to, macromolecules (e.g., enzymes) and surfaces (e.g., electrode surfaces).

For reactive attachment to polymers, substrates, or other carriers, the transition metal complex precursor includes at least one reactive group that reacts with a reactive group on the polymer, substrate, or carrier. Typically, covalent bonds are formed between the two reactive groups to generate a linkage. Examples of such reactive groups and resulting linkages are provided in Table 1, below. Generally, one of the reactive groups is an electrophile and the other reactive group is a nucleophile.

TABLE 1

Examples of Reactive Groups and Resulting Linkages

| First Reactive Group | Second Reactive Group | Resulting Linkage |
|---|---|---|
| Activated ester* | Amine | Carboxamide |
| Acrylamide | Thiol | Thioether |
| Acyl azide | Amine | Carboxamide |
| Acyl halide | Amine | Carboxamide |
| Carboxylic acid | Amine | Carboxamide |
| Aldehyde or ketone | Hydrazine | Hydrazone |
| Aldehyde or ketone | Hydroxyamine | Oxime |
| Alkyl halide | Amine | Alkylamine |
| Alkyl halide | Carboxylic acid | Carboxylic ester |
| Alkyl halide | Imidazole | Imidazolium |
| Alkyl halide | Pyridine | Pyridinium |
| Alkyl halide | Alcohol/phenol | Ether |
| Alkyl halide | Thiol | Thioether |
| Alkyl sulfonate | Thiol | Thioether |
| Alkyl sulfonate | Pyridine | Pyridinium |
| Alkyl sulfonate | Imidazole | Imidazolium |
| Alkyl sulfonate | Alcohol/phenol | Ether |
| Anhydride | Alcohol/phenol | Ester |
| Anhydride | Amine | Carboxamide |
| Aziridine | Thiol | Thioether |
| Aziridine | Amine | Alkylamine |
| Aziridine | Pyridine | Pyridinium |
| Epoxide | Thiol | Thioether |
| Epoxide | Amine | Alkylamine |
| Epoxide | Pyridine | Pyridinium |
| Halotriazine | Amine | Aminotriazine |
| Halotriazine | Alcohol | Triazinyl ether |
| Imido ester | Amine | Amidine |
| Isocyanate | Amine | Urea |
| Isocyanate | Alcohol | Urethane |
| Isothiocyanate | Amine | Thiourea |
| Maleimide | Thiol | Thioether |
| Sulfonyl halide | Amine | Sulfonamide |

*Activated esters, as understood in the art, generally include esters of succinimidyl, benzotriazolyl, or aryl substituted by electron-withdrawing groups such as sulfo, nitro, cyano, or halo; or carboxylic acids activated by carbodiimides.

Transition metal complexes of the present invention can be soluble in water or other aqueous solutions, or in organic solvents. In general, the transition metal complexes can be made soluble in either aqueous or organic solvents by having an appropriate counter ion or ions, X. For example, transition metal complexes with small counter anions, such as F—, Cl—, and Br—, tend to be water soluble. On the other hand, transition metal complexes with bulky counter anions, such as I—, $BF_4$— and $PF_6$—, tend to be soluble in organic solvents. Preferably, the solubility of transition metal complexes of the present invention is greater than about 0.1 M (moles/liter) at 25° C. for a desired solvent.

The transition metal complexes discussed above are useful as redox mediators in electrochemical sensors for the detection of analytes in biofluids. The use of transition metal complexes as redox mediators is described, for example, in U.S. Pat. Nos. 5,262,035, 5,320,725, 5,365,786, 5,593,852, 5,665,222, 5,972,199, 6,134,161, 6,143,164, 6,175,752 and 6,338,790 and U.S. patent application Ser. No. 09/434,026, all of which are incorporated herein by reference. The transition metal complexes described herein can typically be used in place of those discussed in the references listed above, although the results of such use will be significantly enhanced given the particular properties of the transition metal complexes of the present invention, as further described herein.

In general, the redox mediator of the present invention is disposed on or in proximity to (e.g., in a solution surrounding) a working electrode. The redox mediator transfers electrons between the working electrode and an analyte. In some preferred embodiments, an enzyme is also included to facilitate the transfer. For example, the redox mediator transfers electrons between the working electrode and glucose (typically via an enzyme) in an enzyme-catalyzed reaction of glucose. Redox polymers are particularly useful for forming non-leachable coatings on the working electrode. These can be formed, for example, by crosslinking the redox polymer on the working electrode, or by crosslinking the redox polymer and the enzyme on the working electrode.

Transition metal complexes can enable accurate, reproducible and quick or continuous assays. Transition metal complex redox mediators accept electrons from, or transfer electrons to, enzymes or analytes at a high rate and also exchange electrons rapidly with an electrode. Typically, the rate of self exchange, the process in which a reduced redox mediator transfers an electron to an oxidized redox mediator, is rapid. At a defined redox mediator concentration, this provides for more rapid transport of electrons between the enzyme (or analyte) and electrode, and thereby shortens the response time of the sensor. Additionally, the novel transition metal complex redox mediators are typically stable under ambient light and at the temperatures encountered in use, storage and transportation. Preferably, the transition metal complex redox mediators do not undergo chemical change, other than oxidation and reduction, in the period of use or under the conditions of storage, though the redox mediators can be designed to be activated by reacting, for example, with water or the analyte.

The transition metal complex can be used as a redox mediator in combination with a redox enzyme to electrooxidize or electroreduce the analyte or a compound derived of the analyte, for example by hydrolysis of the analyte. The redox potentials of the redox mediators are generally more positive (i.e. more oxidizing) than the redox potentials of the redox enzymes when the analyte is electrooxidized and more negative when the analyte is electroreduced. For example, the redox potentials of the preferred transition metal complex redox mediators used for electrooxidizing glucose with glucose oxidase or PQQ-glucose dehydrogenase as enzyme is between about −200 mV and +200 mV versus a Ag/AgCl reference electrode, and the most preferred mediators have redox potentials between about −200 mV and about +100 mV versus a Ag/AgCl reference electrode.

EXAMPLES OF SYNTHESES OF TRANSITION METAL COMPLEXES

Examples showing the syntheses of various transition metal complexes that are useful as redox mediators are provided below. Unless indicated otherwise, all of the chemical reagents are available from Aldrich Chemical Co, (Milwaukee, Wis.) or other sources. Numerical figures provided are approximate.

Example 1

Synthesis of [Os(Py-MIM)$_2$(MIM)Cl]$^{2+}$2Cl—

By way of illustration, an example of the synthesis of [Os(Py-MIM)$_2$(MIM)Cl]$^{2+}$2Cl—, as illustrated below, is now provided.

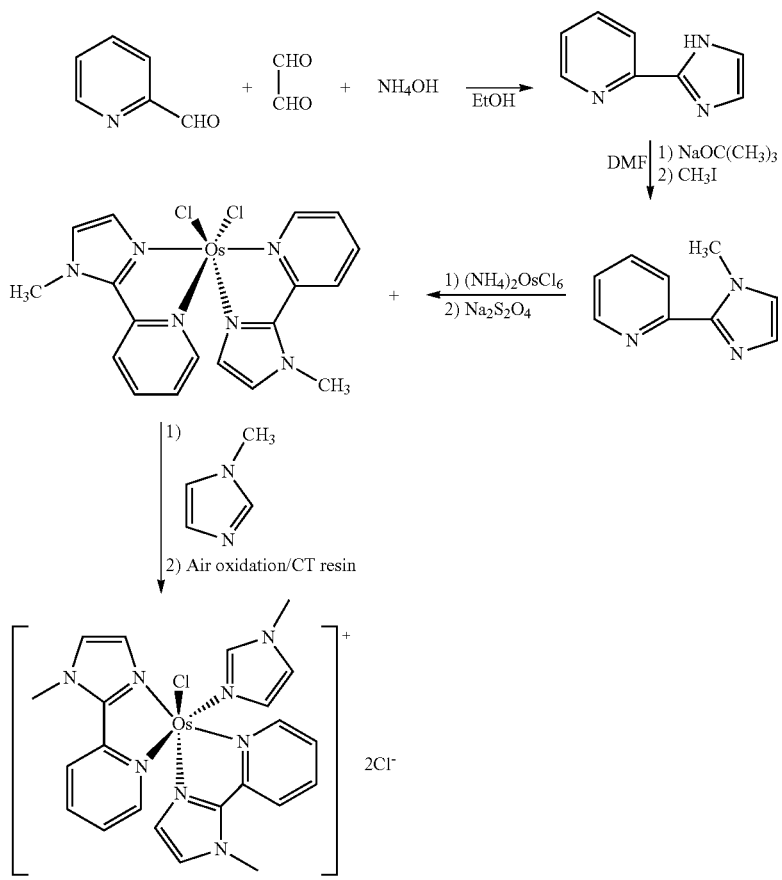

Synthesis of 2-(2-pyridyl)imidazole

A solution of pyridine-2-carboxaldehyde (151.4 g, 1.41 moles) and glyoxal (40% in H$_2$O, 205 mL, 1.79 moles) in 300 mL of ethanol (EtOH) in a three-necked 1 L round-bottom flask fitted with a thermometer and an addition funnel was stirred in an ice bath. When the solution was cooled to below 5° C., concentrated NH$_4$OH (28-30%, 482 mL, 3.93 moles) was added dropwise through the addition funnel. The rate of the addition was controlled so that the temperature of the solution was maintained at below 5° C. After the addition, the stirring of the solution was continued in the ice bath for one hour and then at room temperature overnight. During the stirring process, the solution changed from light yellow to dark brown.

The solution was transferred to a 2 L round bottom flask and the EtOH solvent was removed by rotary evaporation.

The resulting dark viscous material was transferred to a 4 L beaker with 700 mL of EtOAc. 500 mL of saturated NaCl was added and the mixture was stirred for 2 hours. The solution was poured into a 2 L separation funnel and a dark tarry material was discarded. The organic layer was separated from the solution and the aqueous layer was extracted several times with EtOAc (500 mL EtOAc per extraction). The organic layer was then dried with anhydrous $Na_2SO_4$ overnight, whereupon the resulting mixture was gravity filtered, the $Na_2SO_4$ was washed with EtOAc (4×50 mL), and the solution was concentrated to about 300-400 mL by rotary evaporation. The concentrated solution was transferred to a 1 L Erlenmeyer flask and the volume was adjusted with more EtOAc to about 400-500 mL, as necessary. The solution stood at 4° C. for 1-2 days to form large amber crystals. The crystals were collected by suction filtration and washed with cold EtOAc (20-30 mL). The filtrate contained a large amount of product, so further concentration and crystallization procedures were performed. The crystals were combined and dried at 40-45° C. under high vacuum for 2 days. The yield of 2-(2-pyridyl) imidazole was about 75 g.

Synthesis of 1-methyl-2-(2-pyridyl)imidazole

Pyridine-2-carboxaldehyde (50.5 g, 0.47 moles) and glyoxal (40% in $H_2O$, 68.3 mL, 0.60 moles) in 100-150 mL of ethanol (EtOH) in a three-necked 1 L round-bottom flask fitted with a thermometer and an addition funnel were stirred in an ice bath. When the solution was cooled to below 5° C., concentrated $NH_4OH$ (28-30%, 161 mL, 1.31 moles) was added dropwise through the addition funnel. The rate of the addition was controlled so that the temperature of the solution was maintained at below 5° C. After the addition, the stirring of the solution was continued in the ice bath for one hour and then at room temperature overnight. During the stirring process, the solution changed from light yellow to dark brown.

The solution was transferred to a 1 L round bottom flask and the EtOH and $H_2O$ solvent was removed by rotary evaporation at 50° C. The resulting material was dried further at about 50° C. under high vacuum for 24 hours and then dissolved in anhydrous dimethyl formamide (DMF), whereupon the solution was transferred with further DMF (total DMF 450-500 mL) to a three-necked 1 L round bottom flask equipped with a reflux condenser, and then stirred. Sodium t-butoxide (48.9 g, 0.51 moles) was added quickly via a funnel to obtain, with continued stirring for about 1 hour, a dark brown homogeneous solution. Methyl iodide (34.5 mL, 0.56 moles) was then added dropwise via an addition funnel over 1.5-2 hours, resulting in a white precipitate of NaI. The mixture was stirred at room temperature overnight, its color changing from dark brown to light brown. The mixture was then poured into a beaker containing 1.5 mL of EtOAc and suction-filtered using a Buchner funnel to remove the NaI precipitate. The precipitate was washed with additional EtOAc (3×100 mL). The filtrate was transferred to a 2 L round bottom flash and rotary evaporated to remove the EtOAc.

The resulting viscous material was transferred to a 1 L beaker with a minimum amount of EtOAc, which was then removed by rotary evaporation. The remaining DMF was removed by vacuum distillation using a low vacuum diaphragm pump and an oil bath. Upon complete removal of the DMF, the product was distilled at 100-110° C. under high vacuum. The yield of 1-methyl-2-(2-pyridyl)imidazole was about 36 g.

Synthesis of Os(PV-MIM)$_2$Cl$_2$ 1-methyl-2-(2-pyridyl)imidazole (3.4 g, 21.4 mmoles) and ammonium hexachloroosmiate (IV) (4.7 g, 10.7 moles) were combined with anhydrous ethylene glycol (86 mL) in a three-necked 250 mL round bottom flask, fitted with a reflux condenser, immersed in a temperature-controlled oil bath. The reaction mixture was degassed with $N_2$ for about 15 minutes. The mixture was stirred under $N_2$ while the heater was turned on to heat the oil bath, and the reaction proceeded at 130° C. for 2 hours and subsequently at 140° C. for about 28 hours until an intermediate that was formed in the reaction was completely converted to the final product. The solution was cooled to room temperature and then suction-filtered through a fritted funnel into a three-necked 250 mL round bottom flask, whereupon a small amount of orange precipitate left in the funnel was discarded. The solution (solution A) was then degassed with $N_2$ for 15 minutes and kept under $N_2$.

Deionized $H_2O$ (320 mL) was then degassed with $N_2$ in a three-necked 500 mL round bottom flask cooled in an ice/water bath and equipped with a thermometer. After 15 minutes of degassing, sodium hydrosulfite (85%, 9.31 g, 53.5 mmoles) under $N_2$ was added immediately and degassing continued for another 10-15 minutes. The temperature of the solution (solution B) was below 5° C. Solution A was then added via a cannula to solution B under rapid stirring for about 0.5 hour to form a fine dark purple precipitate of Os(Py-MM)$_2$Cl$_2$. Stirring continued under $N_2$ for another 0.5 hour. The resulting suspension was suction-filtered through a 0.4 or 0.3 micron Nylon membrane. The suspension was transferred to the suction funnel via a cannula under nitrogen to minimize air exposure. The dark purple precipitate was then washed with a minimum of ice cold water (2×5 mL). The precipitate was immediately dried by lyophilization for at least 24 hours. The yield of Os(Py-MIM)$_2$Cl$_2$ was about 5.6 g.

Synthesis of [Os(PY-MIM)$_2$(MIM)Cl]$^{2+}$2Cl—

Anhydrous ethanol (1 L) in a 2-L three-necked round bottom flask fitted with a reflux condenser was degassed with $N_2$ for 15 minutes. Os(Py-MIM)$_2$Cl$_2$ (3.1 g, 5.35 mmoles) was added quickly under $N_2$ via a funnel. The suspension was stirred and heated to reflux. 1-methylimidazole (0.43 mL, 5.35 mmoles) was then added at once via a syringe. Reflux continued until the reaction was completed. During the reaction, the solution changed from dark brown to purple-brown. The solution was cooled to room temperature and then suction-filtered through a fritted funnel. The solvent was then removed by rotary evaporation to give the crude product in its reduced form.

The product was transferred with 30-50 mL $H_2O$ to a 400 mL beaker containing about 40 mL AGlx4 chloride resin from Bio-Rad, or preferably, 80 mL Dowex-1-chloride from Aldrich. The mixture was stirred in open air for about 24 hours to convert Os(II) to Os(III). The mixture was then suction-filtered and the resin was washed with $H_2O$ (5×30 mL). The combined filtrate was concentrated to about 50 mL by rotary evaporation at 35° C. under vacuum.

The solution was loaded onto a LH-20 column (2"×22"), which was eluted with $H_2O$. 50 mL fractions were collected and analyzed by CV to find the major purple-brown band associated with the product. Fractions containing pure product were collected and concentrated by rotary evaporation to about 150 mL. The solution was then freeze-dried to give the product. The yield of [Os(Py-MIM)$_2$(MIM)Cl]$^{2+}$2Cl— was about 2.4 g.

As described herein, [Os(Py-MIM)$_2$(MIM)Cl]$^{2+}$2Cl— is a transition metal complex that is particularly useful as a redox mediator.

Example 2

Synthesis of 1-phenyl-2-(2-pyridyl)imidazole

Further by way of illustration, an example of the synthesis of 1-phenyl-2-(2-pyridyl)imidazole, as illustrated below, is now provided. The example demonstrates how a 1-aryl-substituted 2-(2-pyridyl)imidazole is made from 1-(2-pyridyl)imidazole or its derivative, and an iodobenzene derivative (as illustrated) or a bromobenzene derivative.

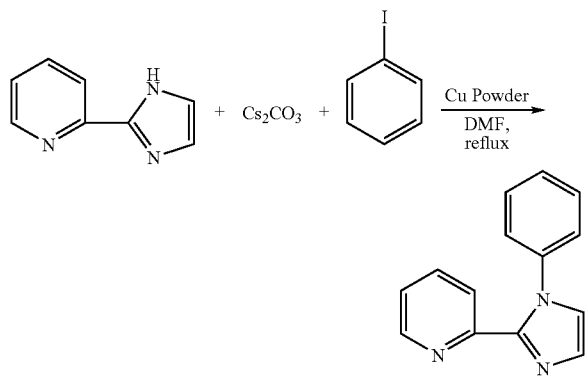

2-(2-pyridyl)imidazole (6.91 g), iodobenzene (1.47 g), $Cs_2CO_3$ (25 g), and copper powder (15 g) were mixed in 60 mL anhydrous DMF in a 250 mL round bottom flask equipped with a magnetic stirrer and a reflux condenser. The mixture is degassed with $N_2$ for 15 minutes at room temperature and then refluxed under $N_2$ in an oil bath for 24 hours. The resulting mixture was cooled to room temperature and suction-filtered to remove the solid byproduct. The filtrate was extracted with EtOAc (3×100 mL). The combined organic layer was washed with $H_2O$ (2×100 mL) and then with saturated NaCl (2×150 mL), and subsequently dried with anhydrous $Na_2SO_4$. Evaporation of the solvent gave crude 1-phenyl-2(2-pyridyl)imidazole. The crude product is generally pure enough to use in making redox mediators, although the crude product may be further purified using a silica gel column and eluting with $MeOH/CHCl_3$.

The 1-phenyl-2-(2-pyridyl)imidazole product described above can be used in the synthesis of a transition metal complex, such as an Osmium complex, in much the same manner 1-methyl-2-(2-pyridyl)imidazole was used in Example 1 above.

Examples of Further Transition Metal Complexes

Further transition metal complexes that serve as redox mediators according to the present invention are provided in Table 2 below, as Mediator Nos. 1-13. The redox potentials ($E_{1/2}$ (mV) relative to a standard Ag/AgCl reference electrode in a pH 7 PBS buffer) associated with these redox mediators are also provided, where available.

Also provided in Tables 3 and 4 are various of these redox mediators and their associated redox potentials and associated slopes, k, of substantially linear plots of collected charge (μC) versus glucose concentration (mg/dL) for a given volume (~315 ηL) of biofluid, such as blood, as further described below. Comparative information for known redox mediators, namely, Comparative Mediator Nos. I, X, XII and XIII is also provided. The slope data in Table 3 and Table 4 concerns redox mediators tested under Condition A and Condition B, respectively, which reflect different ink lots, as now described.

That is, these slope data were obtained from individual tests in which each mediator and an enzyme mixture were coated on a working electrode. The working electrode was made of a conductive ink layered over a plastic substrate. The working electrode was laminated together with a counter/reference electrode, using standard processing known in the art. The counter/reference electrode was made of a Ag/AgCl ink layered over a plastic substrate. Variations are routinely observed in test strip sensors made from different ink lots. Thus, in Table 3, Condition A refers to tests conducted using a series of test strips made from a single lot, and in Table 4, Condition B similarly refers to tests conducted using a series of test strips made from a single lot, different from that associated with Condition A. Thus, comparisons of slope data shown in Table 3 and Table 4 should not be made, while comparisons of slope data shown within either Table 3 or Table 4 are instructive as to mediator performance.

TABLE 2

| | Examples of Low Potential Mediators of the Present Invention | |
|---|---|---|
| Mediator No. | Structure of Mediator | Redox Potential, $E_{1/2}$ (mV) versus Ag/AgCl |
| 1 | [structure] | −164 |

TABLE 2-continued
Examples of Low Potential Mediators
of the Present Invention
| Mediator No. | Structure of Mediator | Redox Potential, $E_{1/2}$ (mV) versus Ag/AgCl |
|---|---|---|
| 2 | 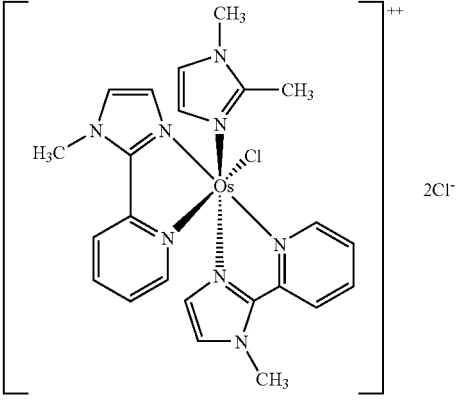 | −168 |
| 3 | 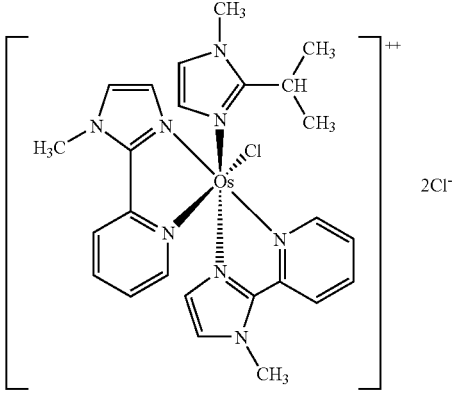 | −150 |
| 4 | 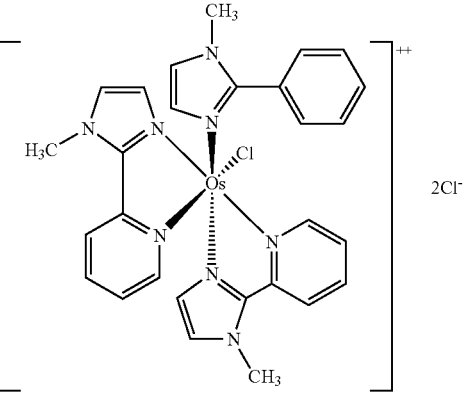 | −172 |

TABLE 2-continued
Examples of Low Potential Mediators
of the Present Invention
| Mediator No. | Structure of Mediator | Redox Potential, $E_{1/2}$ (mV) versus Ag/AgCl |
|---|---|---|
| 5 | 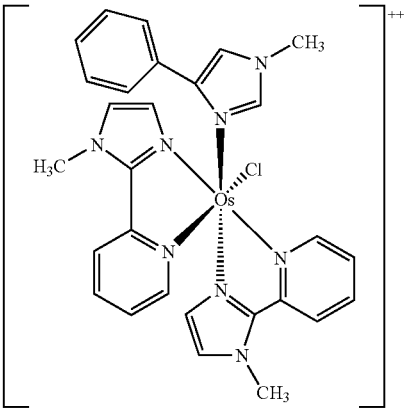 | |
| 6 | 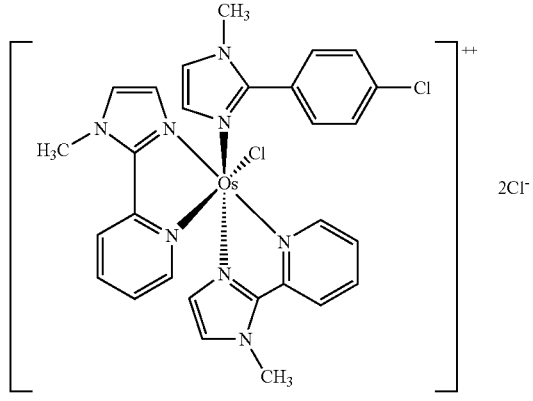 | |
| 7 | 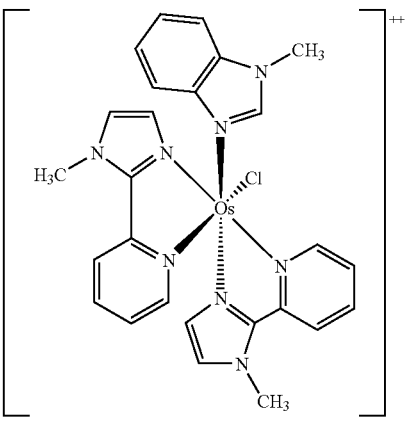 | |

TABLE 2-continued
Examples of Low Potential Mediators
of the Present Invention
| Mediator No. | Structure of Mediator | Redox Potential, $E_{1/2}$ (mV) versus Ag/AgCl |
|---|---|---|
| 8 | 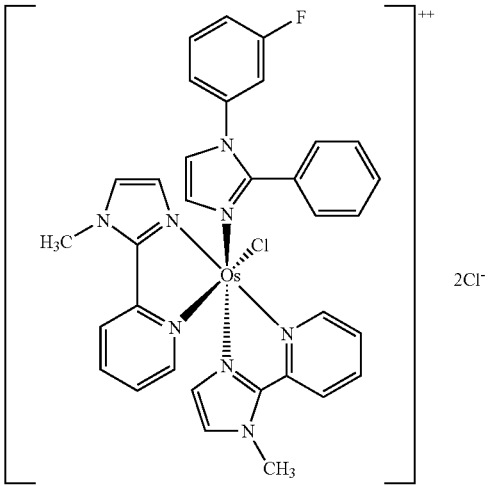 | −139 |
| 9 | 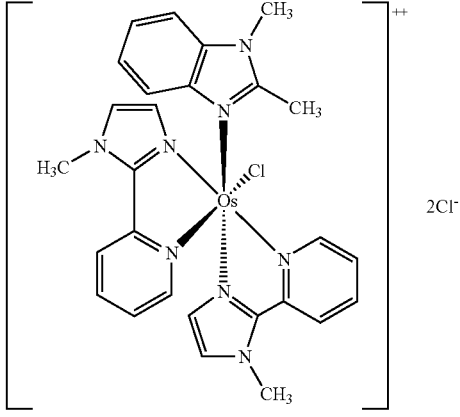 | −124 |
| 10 | 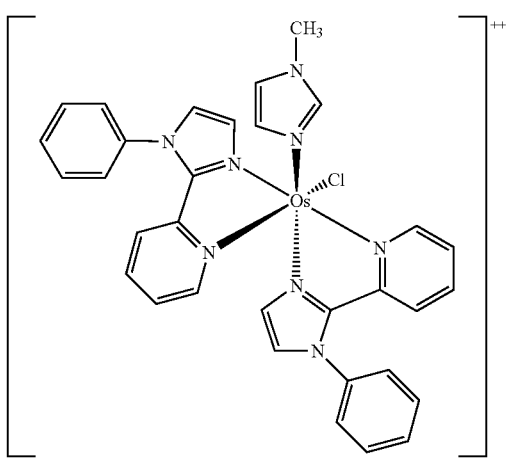 | −117 |

TABLE 2-continued
Examples of Low Potential Mediators of the Present Invention
| Mediator No. | Structure of Mediator | Redox Potential, $E_{1/2}$ (mV) versus Ag/AgCl |
|---|---|---|
| 11 | 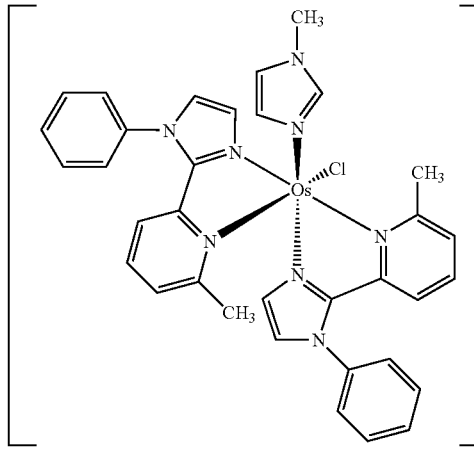 | −130 |
| 12 | 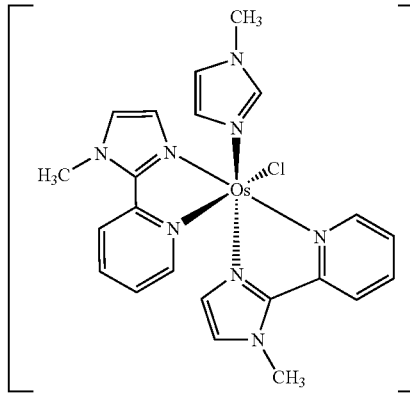 | −166 |
| 13 | 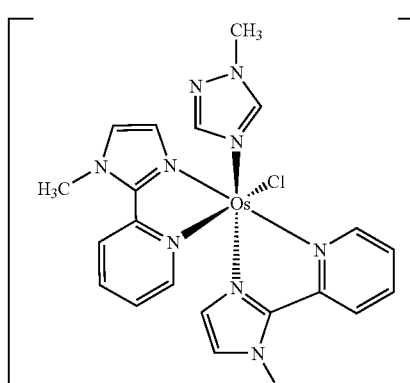 | −88 |

TABLE 3
Examples of Low Potential Osmium Mediators and Known Comparative Mediators and Properties Thereof Under Condition A
| Mediator No. or Comparative Mediator No. | Structure of Mediator or Comparative Mediator | Redox Potential, $E_{1/2}$ (mV) versus Ag/AgCl | Linear Slope, k ($\mu$C/(mg/dL)) |
|---|---|---|---|
| 1 | 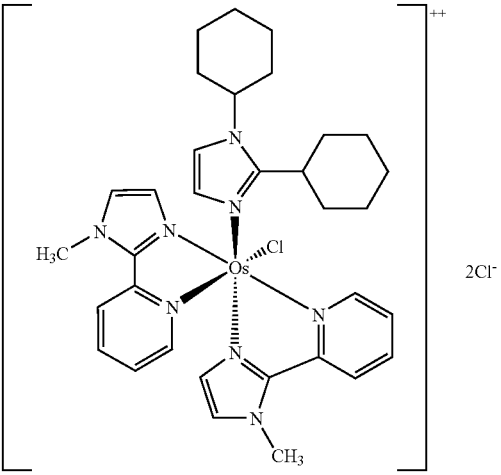 | −164 | 1.52 |
| 2 | 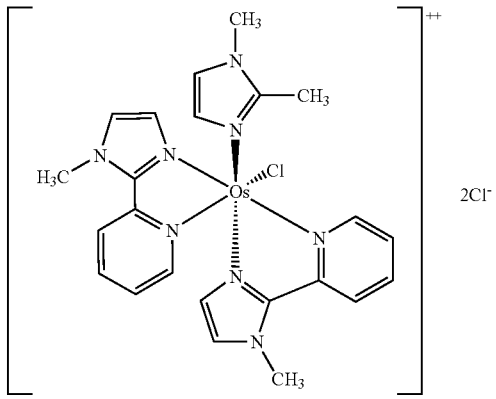 | −168 | 1.49 |
| 3 | 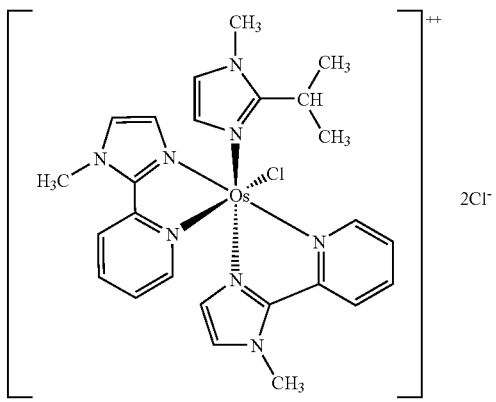 | −150 | 1.46 |

TABLE 3-continued

Examples of Low Potential Osmium Mediators
and Known Comparative Mediators and
Properties Thereof Under Condition A

| Mediator No. or Comparative Mediator No. | Structure of Mediator or Comparative Mediator | Redox Potential, $E_{1/2}$ (mV) versus Ag/AgCl | Linear Slope, k ($\mu$C/(mg/dL)) |
|---|---|---|---|
| 4 | | −172 | 1.49 |
| 11 | | −130 | 1.55 |
| I* | | −110 | 1.14 |

TABLE 3-continued

Examples of Low Potential Osmium Mediators and Known Comparative Mediators and Properties Thereof Under Condition A

| Mediator No. or Comparative Mediator No. | Structure of Mediator or Comparative Mediator | Redox Potential, $E_{1/2}$ (mV) versus Ag/AgCl | Linear Slope, k ($\mu$C/(mg/dL)) |
|---|---|---|---|
| X* | 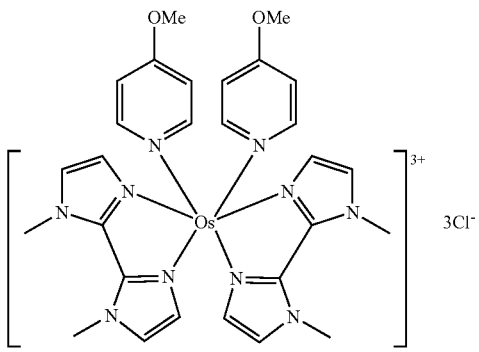 | −125 | 1.05 |

*These known comparative mediators are disclosed in International Publication No. WO 01/36430 A1 and are merely comparative examples herein.

TABLE 4

Examples of Low Potential Osmium Mediators and Known Comparative Mediators and Properties Thereof Under Condition B

| Mediator No. or Comparative Mediator No. | Structure of Mediator or Comparative Mediator | Redox Potential, $E_{1/2}$ (mV) Versus Ag/AgCl | Linear Slope, k ($\mu$C/(mg/dL)) |
|---|---|---|---|
| 8 | 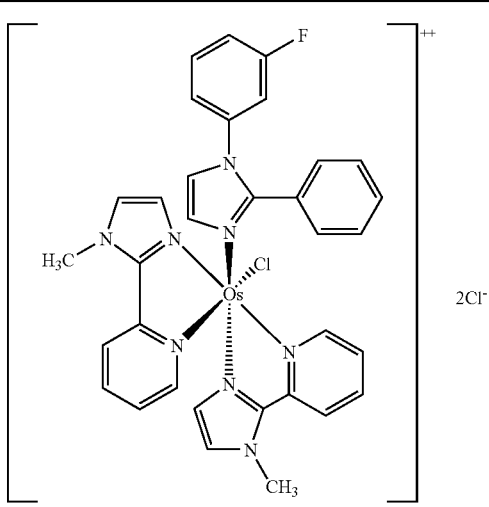 | −139 | 1.73 |

TABLE 4-continued

Examples of Low Potential Osmium Mediators
and Known Comparative Mediators and
Properties Thereof Under Condition B

| Mediator No. or Comparative Mediator No. | Structure of Mediator or Comparative Mediator | Redox Potential, $E_{1/2}$ (mV) Versus Ag/AgCl | Linear Slope, k ($\mu$C/(mg/dL)) |
|---|---|---|---|
| 9 | [structure] | −124 | 1.70 |
| X* | [structure] | −125 | 1.48 |
| XII* | [structure] | −74 | 1.46 |
| XIII* | [structure] | −97 | 1.52 |

TABLE 4-continued

Examples of Low Potential Osmium Mediators
and Known Comparative Mediators and
Properties Thereof Under Condition B

| Mediator No. or Comparative Mediator No. | Structure of Mediator or Comparative Mediator | Redox Potential, $E_{1/2}$ (mV) Versus Ag/AgCl | Linear Slope, k ($\mu$C/(mg/dL)) |
|---|---|---|---|
| IV | 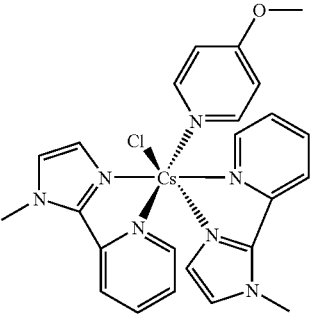 | | |
| XX | 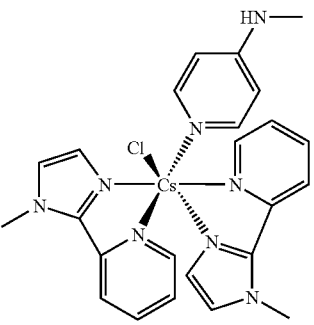 | | |

*These known comparative mediators are disclosed in International Publication No. WO 01/36430 A1 and are merely comparative examples herein.

The transition metal complexes of the present invention are well suited for electrochemical sensing applications, given their particular electrochemical properties. For example, as shown above, the redox potentials of the mediators are generally low, such as in a range of from about 0 mV to about −200 mV relative to a Ag/AgCl reference electrode. These redox potentials are particularly desirable for electrochemical sensing applications, being in a range at which the kinetics of the mediators is fast and the electrochemical activity of potentially interfering species is minimized. Mediator Nos. 1-13 thus exemplify electrochemically desirable mediators according to the present invention.

The identity of the potentially interfering species just described depends on the particular electrochemical sensing application. Merely by way of example, when the electrochemical sensing application concerns the biofluid, blood, potentially interfering species include ascorbic acid, acetaminophen, and uric acid. Mediator Nos. 1-13 exemplify electrochemically desirable mediators that operate at potentials suitable for minimizing the electrochemical activity of such potentially interfering species, while not sacrificing mediator efficiency.

Additionally, the transition metal complexes of the present invention are particularly effective redox mediators in electrochemical sensing applications, given their enhanced ability to collect charge at the working electrode, which in turn enhances the sensitivity of the sensor to the concentration of the analyte being sensed. By way of example, in the general operation of an electrochemical biosensor, such as a glucose sensor, the reduced enzyme, glucose oxidase or glucose dehydrogenase, transfers its electrons to the working electrode via a particular process. In that process, the oxidized form of the redox mediator interacts with the reduced enzyme, thereby receiving an electron and becoming reduced. The reduced mediator travels to the surface of the working electrode, typically by random diffusion, whereupon it transfers the collected electron to the electrode, thereby becoming oxidized.

Ideally, because each glucose molecule loses two electrons in the above-described process, the total amount of electrons or charge collected at the working electrode should be equal to two times the number of glucose molecules oxidized. In practice, however, the total amount of charge collected is almost always less than the ideal or theoretical amount because the electrons may be "lost" during transfer from the enzyme to the electrode. For example, the reduced enzyme may transfer the electrons to oxygen or other chemical species, rather than to the redox mediator. An efficient redox mediator should thus compete favorably for electrons from the enzyme.

Further, ideally, once the redox mediator receives an electron from the enzyme, it should not transfer the electron to another oxidative species, such as oxygen or other chemicals present in the sensor, before being oxidized on the working electrode. A good mediator should thus compete favorably for electrons from the reduced enzyme, as described above, and be substantially chemically inert during its random diffusion to the working electrode whereupon it is oxidized.

An efficient mediator is particularly important in coulometry-based electrochemical biosensing, in which detection of the bioanalyte is based on the total amount of charge collected at the working electrode for a given volume of biofluid. When greater charge is collected at the working electrode, the sensor is advantageously more sensitive. For a coulometry-based glucose sensor, for example, the sensitivity of the sensor may be characterized by the slope value of a linear plot of charge versus glucose concentration as defined by the equation y=kx+b, where y is the collected charge in μC for a given volume of biofluid, k is the slope in μC/(mg/dL), x is the glucose concentration in mg/dL, and b is the intercept based on background charge. As demonstrated above, mediators of the present invention that have a negatively charged ligand, such as Mediator Nos. 1-13 that have a chloride ligand, have associated slope values that are significantly higher (for example, about 28% to about 48% higher per Table 3, and about 11% to about 18% higher per Table 4) than those of mediators that have heterocyclic nitrogen-containing ligands surrounding the metal redox center, as exemplified by Comparative Mediator Nos. I, X, XII and XIII.

The above-described data demonstrate favorable properties of transition metal complexes that make these complexes particularly desirable redox mediators. In electrochemical sensing applications, such as the electrochemical sensing of glucose, the transition metal complexes effectively collect electrons from the reduced enzyme and effectively retain the collected electrons prior to delivering them to the working electrode.

As described herein, the transition metal complexes of the present invention are usefully employed as redox mediators in electrochemical sensors. These mediators have very fast kinetics, such that electron exchange between such a mediator and the enzyme and/or the working electrode in the sensor device is rapid, and more particularly, rapid enough to facilitate the transfer of electrons to the working electrode that might otherwise be transferred to another electron scavenger, such as oxygen. The electron-transfer efficiency of a mediator of Formula 1 is enhanced when $L_2$ is a negatively charged ligand, such as a chloride ligand, as demonstrated by the desirable slope values, k, listed above for Mediator Nos. 1-13. By way of comparison, a mediator having a neutral ligand, $L_2$, such as a heterocyclic nitrogen-containing ligand, is less able to transfer electrons from the enzyme to the working electrode, as reflected by the lower slope values listed above for Comparative Mediator Nos. I, X, XII and XIII.

The transition metal complex mediators of the present invention are also quite stable in terms of chemical reactivity with respect to chemical species other than the enzyme and the electrode surface. By way of example, the chemical stability of a mediator of the present invention is such that preferably the predominant, or most preferably the only, reactions in which it participates involves the above-described, electron-transfer reaction between the mediator and the enzyme and the electrochemical redox reaction at the working electrode. This chemical stability may be enhanced when a mediator of Formula 1, wherein $L_2$ is a negatively charged monodentate ligand, has a "bulky" chemical ligand, $L_1$, that spatially or stereochemically shields the redox center, such as $Os^{2+/3+}$, and thereby, reduces undesirable chemical reactivity beyond the fundamentally desired chemical and electrochemical activity. Mediator Nos. 1-13, above, are particular examples of such "bulked", chemically stable mediators of the present invention.

Further by way of example, the thermal and photochemical stability of a mediator of the present invention is preferably such that the mediator is temperature- and light-stable, respectively, under typical use, storage and transportation conditions. For example, mediators of the present invention may be easily handled under normal lighting conditions and may have a shelf life of at least about 18 months at about room temperature, and at least about 2 weeks at about 57° C. Mediator Nos. 1-13, above, are particular examples of such thermally and photochemically stable mediators of the present invention.

Mediators of the present invention have desirable redox potentials in a range at which the electron-transfer kinetics is optimized, or maximized, and the effect of common interfering species present in biofluid is minimized. Mediator Nos. 1-13, above, are particular examples of mediators of suitable redox potential.

The transition metal complex mediators of the present invention also have desirable solubility properties, generally having a solubility of greater than about 0.1 moles/liter at 25° C. for a desired solvent, which is typically an aqueous or a water-miscible solvent. Advantageously, one need only adjust the counter ion or ions, X, of Formula 1, to obtain a desirable solubility for the solvent of choice, be it aqueous or organic.

In summary, the present invention provides novel transition metal complexes that are particularly useful as redox mediators in electrochemical sensing applications. The preferred redox mediators exchange electrons rapidly with enzymes and working electrodes, are stable, are readily synthesized, and have redox potentials that are tailored for the electrooxidation of a variety of analytes, such as those in various biological fluids within the human body. While mediators of the present invention have been described for the most part in terms of glucose sensing, they are useful for the sensing of other analytes, such as lactic acid for example. Generally, if the redox potential of the enzyme used in a particular analyte-sensing application is negative relative to the redox potential of the mediator, the mediator is suitable for that analyte-sensing application. The advantageous properties and characteristics of the transition metal complexes of the present invention make them ideal candidates for use in the electrochemical sensing of glucose, an application of particular importance in the diagnosis and monitoring of diabetes in human populations.

Various aspects and features of the present invention have been explained or described in relation to beliefs or theories, although it will be understood that the invention is not bound to any belief or theory. Further, various modifications, equivalent processes, as well as numerous structures to which the present invention may be applicable will be readily apparent to those of skill in the art to which the present invention is directed upon review of the instant specification. Although the various aspects and features of the present invention have been described with respect to various embodiments and specific examples herein, it will be understood that the invention is entitled to protection within the full scope of the appended claims.

The invention claimed is:

1. A transition metal complex having the formula:

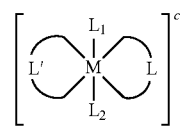

wherein c is a negative, neutral, or positive charge represented by −1 to −5, 0, or +1 to +5, inclusive, respectively;
d is a number of counter ions, X, from 0 to 5, inclusive;
M is cobalt, iron, osmium, ruthenium, or vanadium;

$L_1$ has the formula:

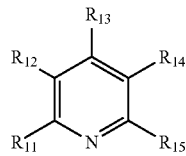

wherein $R_{11}$, $R_{12}$, $R_{14}$ and $R_{15}$ are independently —H, —F, —Cl, —Br, —I, —NO$_2$, —CN, —CO$_2$H, —OH, —NH$_2$, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl and $R_{13}$ is a C1-C2 alkylamino;
$L_2$ is a negatively charged ligand; and
L and L' are independently:

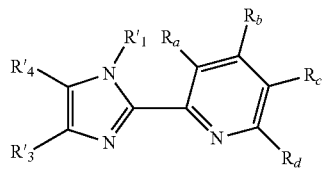

wherein $R'_1$ is a substituted or an unsubstituted alkyl, alkenyl or aryl;
each of $R_a$ and $R_b$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl;
each of $R_c$ and $R_d$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxyfamino, alkoxylamino, alkylthio, alkenyl, aryl, or alkyl, or a combination of Rc and Rd forms a saturated or an unsaturated 5- or 6-membered ring; and
each of $R'_3$ and $R'_4$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl, or a combination of $R'_3$ and $R'_4$ forms a saturated or an unsaturated 5- or 6-membered ring.

2. The transition metal complex of claim 1, wherein $R_{13}$ is a C1 alkylamino.

3. A method for monitoring the concentration of an analyte in biological fluid, the method comprising:
applying a sample containing the analyte to an electrochemical sensor, the electrochemical sensor comprising:
a working electrode, wherein the working electrode comprises a transition metal complex having the formula:

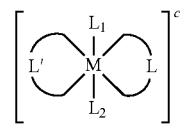

wherein c is a negative, neutral, or positive charge represented by −1 to −5, 0, or +1 to +5, inclusive, respectively;
d is a number of counter ions, X, from 0 to 5, inclusive;
M is cobalt, iron, osmium, ruthenium, or vanadium;
$L_1$ has the formula:

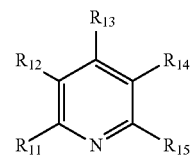

wherein $R_{11}$, $R_{12}$, $R_{14}$ and $R_{15}$ are independently —H, —F, —Cl, —Br, —I, —NO$_2$, —CN, —CO$_2$H, —OH, —NH$_2$, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl and $R_{13}$ is C1-C2 alkylamino;
$L_2$ is a negatively charged ligand; and
L and L' are independently:

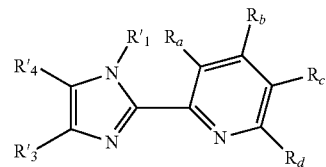

wherein $R'_1$ is a substituted or an unsubstituted alkyl, alkenyl or aryl;
each of $R_a$ and $R_b$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl;
each of $R_c$ and $R_d$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxyfamino, alkoxylamino, alkylthio, alkenyl, aryl, or alkyl, or a combination of Rc and Rd forms a saturated or an unsaturated 5- or 6-membered ring; and
each of $R'_3$ and $R'_4$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl, or a combination of $R'_3$ and $R'_4$ forms a saturated or an unsaturated 5- or 6-membered ring; and an analyte responsive enzyme; and a counter electrode; and determining the concentration of an analyte in the sample.

4. The method of claim 3 wherein the analyte is glucose.

5. The method of claim 3 wherein the analyte is a ketone.

6. A transition metal complex having the formula:

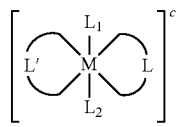

wherein c is a negative, neutral, or positive charge represented by −1 to −5, 0, or +1 to +5, inclusive, respectively;

d is a number of counter ions, X, from 0 to 5, inclusive;

M is cobalt, iron, osmium, ruthenium, or vanadium;

$L_1$ has the formula:

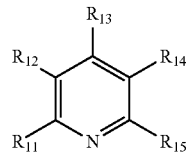

wherein $R_{11}$, $R_{12}$, $R_{14}$ and $R_{15}$ are independently —H, —F, —Cl, —Br, —I, —NO$_2$, —CN, —CO$_2$H, —OH, —NH$_2$, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl and $R_{13}$ is a C1-C2 alkoxy;

$L_2$ is a negatively charged ligand; and

L and L' are independently:

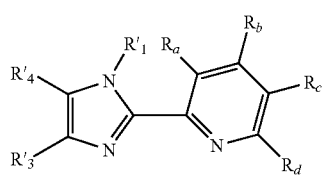

wherein $R'_1$ is a substituted or an unsubstituted alkyl, alkenyl or aryl;

each of $R_a$ and $R_b$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl;

each of $R_c$ and $R_d$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxyfamino, alkoxylamino, alkylthio, alkenyl, aryl, or alkyl, or a combination of Rc and Rd forms a saturated or an unsaturated 5- or 6-membered ring; and each of $R'_3$ and $R'_4$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl, or a combination of $R'_3$ and $R'_4$ forms a saturated or an unsaturated 5- or 6-membered ring.

7. The transition metal complex of claim 6, wherein $R_{13}$ is a C1 alkoxy.

8. A method for monitoring the concentration of an analyte in biological fluid, the method comprising:

applying a sample containing the analyte to an electrochemical sensor, the electrochemical sensor comprising:

a working electrode, wherein the working electrode comprises a transition metal complex having the formula:

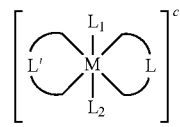

wherein c is a negative, neutral, or positive charge represented by −1 to −5, 0, or +1 to +5, inclusive, respectively;

d is a number of counter ions, X, from 0 to 5, inclusive;

M is cobalt, iron, osmium, ruthenium, or vanadium;

$L_1$ has the formula:

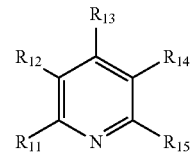

wherein $R_{11}$, $R_{12}$, $R_{14}$ and $R_{15}$ are independently —H, —F, —Cl, —Br, —I, —NO$_2$, —CN, —CO$_2$H, —OH, —NH$_2$, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl and $R_{13}$ is a C1-C2 alkoxy;

$L_2$ is a negatively charged ligand; and

L and L' are independently:

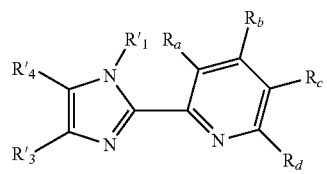

wherein $R'_1$ is a substituted or an unsubstituted alkyl, alkenyl or aryl;

each of $R_a$ and $R_b$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl;

each of $R_c$ and $R_d$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxyfamino, alkoxylamino, alkylthio, alkenyl, aryl, or alkyl, or a combination of Rc and Rd forms a saturated or an unsaturated 5- or 6-membered ring; and each of $R'_3$ and $R'_4$ is independently —H, —F, —Cl, —Br, —I, —NO$_2$, —CN, —CO$_2$H, —SO$_3$H, —NHNH$_2$, —SH, —OH, —NH$_2$, or substituted or unsubstituted alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxylamino, alkylthio, alkenyl, aryl, or alkyl, or a combination of $R'_3$ and $R'_4$ forms a saturated or an unsaturated 5- or 6-membered ring; and an analyte responsive enzyme; and a counter electrode; and determining the concentration of an analyte in the sample.

9. The method of claim 8, wherein the analyte is glucose.

10. The method of claim 8, wherein the analyte is a ketone.

* * * * *

UNITED STATES PATENT AND TRADEMARK OFFICE
CERTIFICATE OF CORRECTION

PATENT NO.       : 8,070,934 B2
APPLICATION NO.  : 11/933219
DATED            : December 6, 2011
INVENTOR(S)      : Fei Mao et al.

Page 1 of 1

It is certified that error appears in the above-identified patent and that said Letters Patent is hereby corrected as shown below:

In column 9, please replace structure 14 with the following:

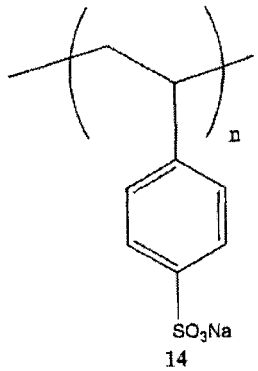

In Table 4, at columns 31-32, please replace structure XIII with the following structure:

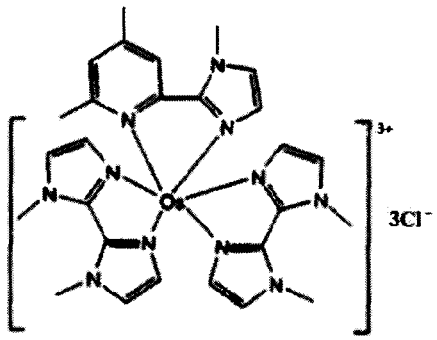

In claims 1, 3, 6 and 8, please add "dX" outside the brackets of the recited transition metal complex formula, as shown in the following:

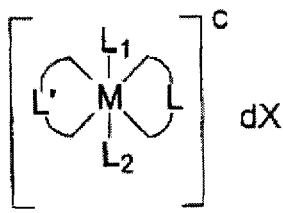

Signed and Sealed this
Fourth Day of September, 2012

David J. Kappos
*Director of the United States Patent and Trademark Office*